(12) United States Patent
Barclay

(10) Patent No.: US 9,717,499 B2
(45) Date of Patent: Aug. 1, 2017

(54) APPARATUS FOR APPLYING A BAND TO A HAEMORRHOID

(71) Applicant: Phillip Barclay, Abingdon (GB)

(72) Inventor: Phillip Barclay, Abingdon (GB)

( * ) Notice: Subject to any disclaimer, the term of this patent is extended or adjusted under 35 U.S.C. 154(b) by 96 days.

(21) Appl. No.: 14/438,027

(22) PCT Filed: Apr. 23, 2013

(86) PCT No.: PCT/GB2013/051021
§ 371 (c)(1),
(2) Date: Apr. 23, 2015

(87) PCT Pub. No.: WO2014/072676
PCT Pub. Date: May 15, 2014

(65) Prior Publication Data
US 2015/0272587 A1    Oct. 1, 2015

(30) Foreign Application Priority Data

Nov. 7, 2012 (GB) .................................. 1220030.9

(51) Int. Cl.
*A61B 17/10* (2006.01)
*A61B 17/12* (2006.01)
(Continued)

(52) U.S. Cl.
CPC .. *A61B 17/12009* (2013.01); *A61B 17/12013* (2013.01); *A61B 2017/0053* (2013.01);
(Continued)

(58) Field of Classification Search
CPC .......... A61B 2017/12018; A61B 17/12; A61B 17/12013; A61B 2017/0053; A61B 17/12009; A61B 17/1222

USPC .................................................. 606/140, 142
See application file for complete search history.

(56) References Cited

U.S. PATENT DOCUMENTS

| 4,257,419 A | 3/1981 | Goltner et al. |
| 5,643,290 A * | 7/1997 | Clark ........................ A61F 5/41 606/140 |

(Continued)

OTHER PUBLICATIONS

PCT International Search Report and Written Opinion corresponding to International Application No. PCT/GB2013/051021; Date of mailing of the International Search Report and Written Opinion: Oct. 1, 2013 (13 pages).

(Continued)

*Primary Examiner* — Katherine M Shi
(74) *Attorney, Agent, or Firm* — Myers Bigel, P.A.

(57) ABSTRACT

A magazine (200;400) for dispensing at least one band (106) onto the tip of a haemorrhoid ligator (100), the magazine (200; 400) comprising at least one expander receiving a respective band, the expander being arranged to expand the band and push it onto the tip (104) of the ligator (100) as the tip (104) is inserted into the magazine (200; 400). The only action required by the medical practitioner to load the band (106) onto the ligator (100) from the magazine (200;400) is to push the tip (104) of the ligator (100) inside the magazine (200; 400) whereupon the band (106) is expanded, pushed into place and is ready for immediate discharge. Therefore the magazine (200; 400) provides a medical practitioner with an easy way to load a haemorrhoid ligator (100).

9 Claims, 8 Drawing Sheets

(51) Int. Cl.
*A61B 17/00* (2006.01)
*A61B 17/30* (2006.01)
*A61B 50/00* (2016.01)
*A61B 50/30* (2016.01)

(52) U.S. Cl.
CPC ............... *A61B 2017/00566* (2013.01); *A61B 2017/12018* (2013.01); *A61B 2017/308* (2013.01); *A61B 2050/0065* (2016.02); *A61B 2050/3008* (2016.02)

(56) References Cited

U.S. PATENT DOCUMENTS

| | | | | |
|---|---|---|---|---|
| 5,741,273 | A * | 4/1998 | O'Regan | A61B 17/12013 606/1 |
| 6,482,213 | B1 * | 11/2002 | Riza | A61B 17/12 606/140 |
| 2002/0111639 | A1 | 8/2002 | Armstrong | |
| 2006/0058818 | A1 | 3/2006 | Liberatore et al. | |
| 2006/0259041 | A1 * | 11/2006 | Hoffman | A61B 17/12013 606/139 |
| 2012/0009295 | A1 * | 1/2012 | Bastia | A61B 17/12013 425/395 |
| 2012/0078272 | A1 * | 3/2012 | Smith | A61B 17/12009 606/140 |

OTHER PUBLICATIONS

Search Report corresponding to GB1220030.9; Date of Search Report: Jan. 29, 2013 (1 page).

\* cited by examiner

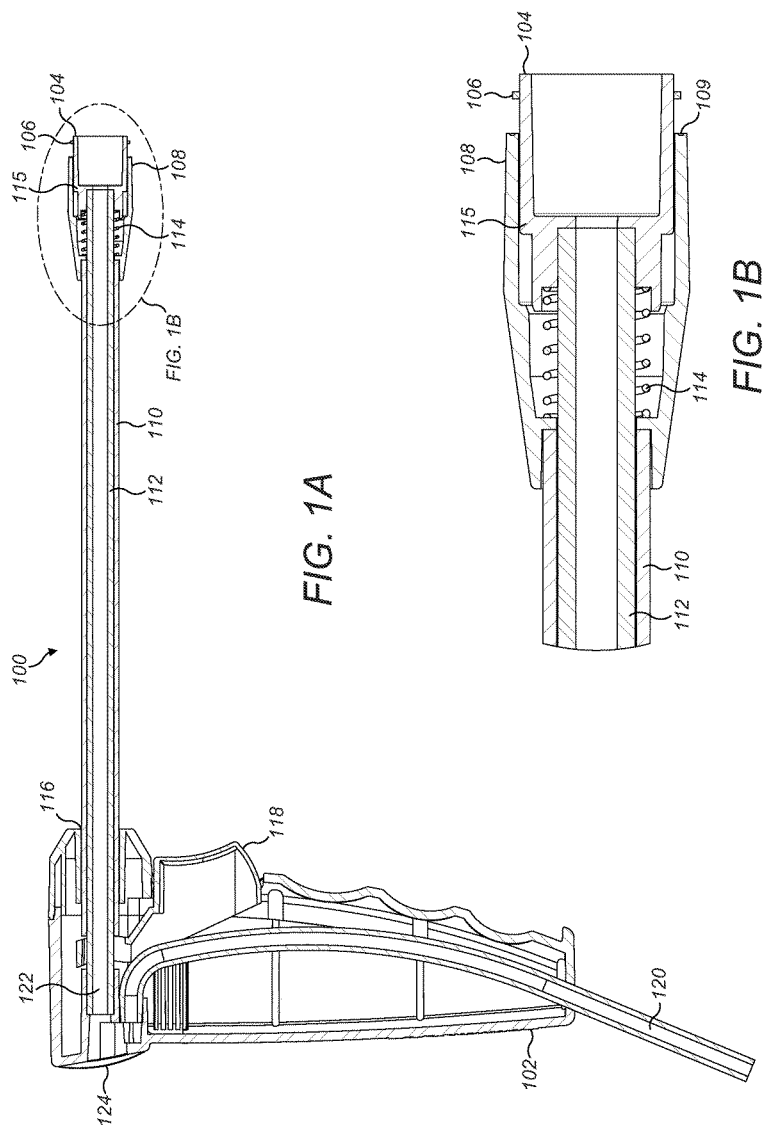

APPARATUS FOR APPLYING A BAND TO A HAEMORRHOID

RELATED APPLICATIONS

This application is a 35 U.S.C. §371 national stage application of PCT Application No. PCT/GB2013/051021, filed on Apr. 23, 2013, which claims priority from Great Britain Patent Application No. 1220030.9, filed Nov. 7, 2012, the disclosures of which are incorporated herein by reference in their entireties. The above-referenced PCT International Application was published in the English language as International Publication No. WO 2014/072676 A1 on May 15, 2014.

The present invention relates to an apparatus for applying a band to a haemorrhoid.

When haemorrhoids become swollen, they can cause discomfort to the affected person or animal and so may need to be removed. One way a haemorrhoid is removed is by strangulating its blood supply by applying a band around the base of it using a ligator. The band, when applied, causes the tissue of the haemorrhoid to die. After a few days the dead tissue, together with the band, fall away from the surrounding healthy tissue and are excreted.

An example apparatus for applying a band around a haemorrhoid is shown in U.S. Pat. No. 4,257,419. The ligator therein shown is loaded with a band using the cone shaped attachment shown in FIGS. 4 and 5 of the document. The band is rolled up the cone by band onto the end of the ligator. Once applied, the band is then held in a highly stretched state around the end of the ligator, ready for application around a haemorrhoid after the cone shaped attachment has been removed.

Loading the ligator in this way is fiddly given the size of the band which is used. Often when applying the band up the cone, the band may ping off half way up. The band may also break during its movement up the cone, due to the uneven forces applied by the band of the medical practitioner applying the band.

One way to prevent this problem is to supply the ligator preloaded with a band. The difficulty with this solution is that the band, which is held in an expanded state around the end of the ligator, may be held around the end of the ligator for some time before the ligator is used. In this time, the band may lose some of its elasticity whilst left in its expanded state. When the band is then used, it may not effectively apply around the haemorrhoid and accordingly fail to strangulate its blood supply.

In some instances, it may be necessary to remove more than one haemorrhoid on a human or animal. One solution to this is to preload the ligator with several bands—one above the other. As each band is deployed, the next band is then positioned to be used. An example of this setup is shown in US 2002/0111639. This solution however means that all the bands on the ligator must be stored in a highly stretched condition until use. The time spent in this isolated stretched condition may make the band flaccid and result in poor application around the haemorrhoid when it is deployed.

Accordingly, the present invention provides a magazine for dispensing at least one band onto the tip of a haemorrhoid ligator according to claim 1.

With this arrangement, the only action required by the medical practitioner to load the band onto the ligator from the magazine is to push the tip of the ligator inside the magazine whereupon the band is expanded, pushed into place and is ready for immediate discharge. Therefore the magazine provides a medical practitioner with an easier way to load a ligator than before, which does not require him to manually roll the band onto the tip of the ligator by band. The use of the magazine also allows the band to be applied much more effectively, and with less chance of breaking during its application, onto the ligator.

The magazine also ensures that each stored band is in a relatively unexpanded position in the reloader, meaning that the elasticity in each band is preserved for as long as possible.

The magazine may comprise a plurality of expanders. By having a plurality of expanders, the reloader can be used to quickly reload the ligator after it has dispensed the first band, thus reducing the length of procedures where more than one haemorrhoid requires banding.

The or each expander may comprise any suitable configuration for applying the band onto the ligator. It may, for example, comprise two separate mechanisms: a band expanding mechanism, and a pushing mechanism for applying the expanded band onto the tip of the ligator In its simplest form, the or each expander may comprise an expansion cone and a band feeder, wherein the band feeder is arranged to push the band along an outer surface of the expansion cone upon insertion of the tip.

In one embodiment, the or each band feeder may comprise a plurality of resilient prongs, wherein each prong rests against, and is deflected by, the outer surface of the expansion cone as the tip is inserted into the magazine.

Each prong may comprise a foot for holding the band as it is pushed, wherein the foot is the part of the prong which rests against the outer surface of the expansion cone.

In an alternative embodiment, the or each band feeder may comprise a plate which is configured to slide with respect to a slot in the expansion cone, the plate having an end which engages with the band as it is pushed.

This sliding action provides a better way of pushing the band onto the ligator, as the end of the or each plate acts a cam surface which forces the band along the outer surface of the expansion cone. The arrangement also allows the band feeder to be formed integrally with the magazine, such that both components can be formed together as a single part.

The slot may be located in a fin of the expansion cone. Alternatively, the slot may be formed into a solid cylindrical component inside the outer surface of the expansion cone.

The end of the or each plate may be shaped to guide the band along the outer surface of the expansion cone.

As the plate passes through the slot of the expansion cone, the band is forced along the outer surface of the expansion cone by the guiding end of the plate.

In either embodiment the face of the outer surface of the expansion cone furthest from the band feeder may be tapered in an opposing direction to the outer surface of the expansion cone.

When the band is pushed onto the tapered face, the taper assists with the movement of the band onto the tip of the ligator.

The magazine may be provided in combination with a sterile package, wherein the magazine is sealed within the sterile package. This has the advantage that the magazine is supplied in a sterile condition and is available for immediate use.

According to a second aspect of the invention, there is provided a haemorrhoid ligator suitable for applying a band around a haemorrhoid. The ligator includes an inner element with a cup shaped distal end, the inner surface of which is configured to be placed over the haemorrhoid and the outer surface of which is configured to receive the band; a sleeve which is positioned around the inner element; a band applicator at the distal end of the sleeve; and an elastic member which is connected between the inner element and the band applicator. In use, the sleeve is arranged to be distally moved to move the band applicator distally from an initial position to a second position nearer to the distal end of the cup shaped end of the inner element, so as to push the band off the distal end of the cup shaped end, and place the elastic member in a compressed state, such that the elastic member provides a biasing force to restore the sleeve and band applicator back to their initial positions when the sleeve is released.

By having the sleeve and the band applicator moved back to their initial positions automatically after the band has been applied, the ligator can be reloaded with a new band to allow the ligator to be reused.

The interior of the cup shaped end may be connected to a vacuum source. In this way, when the cup shaped end of the ligator is placed near the haemorrhoid, the interior of the cup can be placed in a higher vacuum condition to help attract the haemorrhoid inside the cup.

The inner element may comprise an open ended tube which has a distal end in fluid communication with the interior of the cup shaped end, and a proximal end in fluid communication with the vacuum source. In this way, no external pressure lines are required between the vacuum source and the cup shaped end The pressure of the interior of the cup may be controllable by an atmospheric opening located between the interior of the cup and the vacuum source. Ideally, the opening should be controlled by the user operating the ligator, and should be easily accessible to this operator. Preferably the opening should be controllable with the same band as that which is operating the ligator.

The ligator may further comprise a trigger located at the proximal end of the ligator. The trigger facilitates the distal movement of the band applicator.

In some instances, the band applicator of the ligator may abut a proximal end of the cup shaped end when the sleeve is in the second position. In this way, the abutment provides an indication to the medical practitioner, which he should feel, that the band applicator is in its most distal position and that the band has therefore been applied. This feeling by the practitioner is particularly important as the end of the ligator may not be visible during use to provide a visual indication to the practitioner that the band has been applied.

The ligator may be provided in combination with a sterile package, wherein the ligator is sealed within the sterile package. This has the advantage that the ligator is supplied in a sterile condition and is available for immediate use.

Thus the two aspects of the present invention together provide a ligator which is reloadable and a corresponding separate magazine reloader which is configured to reload the ligator.

Both the ligator and the reloader will now be described in detail, by way of example only, with reference to the accompanying drawings, in which:

FIG. 1A shows a cross section of a band ligator. FIG. 1B shows a close up view of the distal end of the ligator.

Figure 2C:
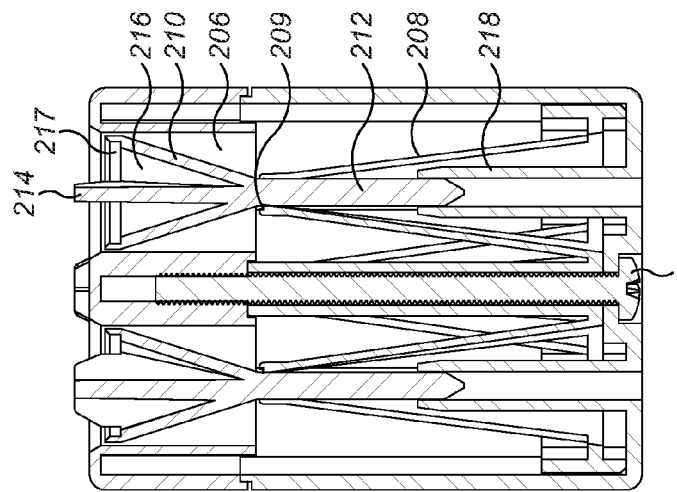
FIGS. 2A-2D show respective side, top end, cross section, and expanded perspective views of a reloader configured to be used with the band ligator of FIGS. 1A-1B.
Figure 2B:
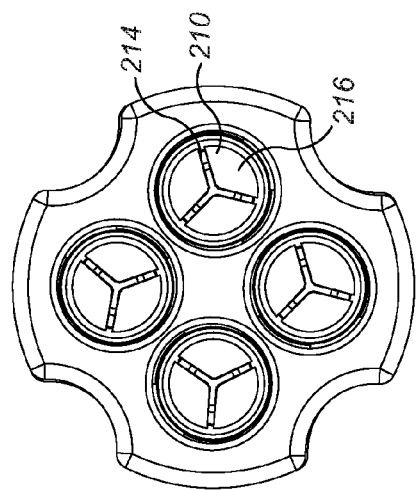
Figure 2A:
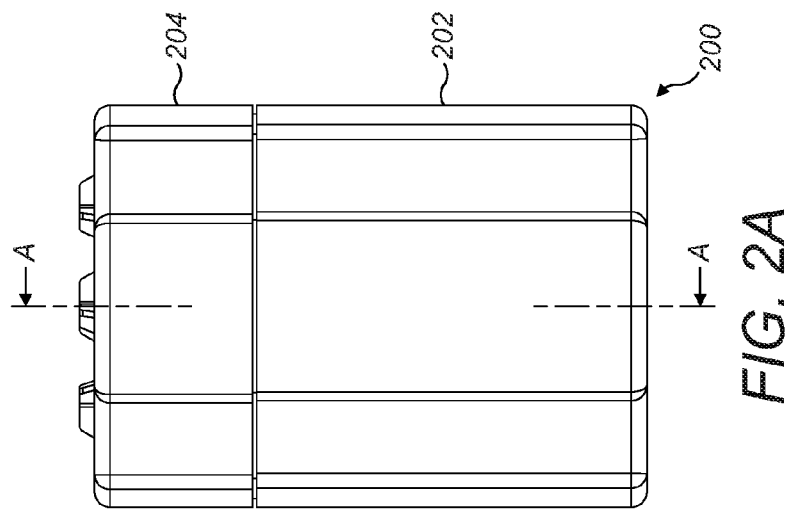

The band ligator 100 shown in FIG. 1A is held by a medical practitioner by the handle 102 located at its proximal end. The distal end of the ligator is formed in the shape of a cup 104 whose outer surface accommodates a band 106 which is preferably latex free (to comply with UK health laws).

Next to the cup is a band applicator 108 whose movement is controlled by a sleeve 110 which is slidable around an inner element 112, which the cup 104 forms a part thereof. Biasing the band applicator 108 in the proximal direction is an elastic member 114 which is shown in FIGS. 1A and 1B as a spring.

The sleeve 110 and the inner element 112 are positioned through a hole 116 in the handle 102. Also positioned in the handle 102 is a trigger 118.

To operate the ligator 100, the practitioner places the cup shaped end 104 of the ligator over the haemorrhoid and pulls the trigger 118. Movement of the trigger 118 results in the sleeve 110 sliding distally over the inner element 112 and compressing the elastic member 114. The distal movement of the sleeve forces the band applicator 108, and ultimately the band 106, to move in the same distal direction. Further depression of the trigger results in the sleeve and band applicator moving to such a degree that the band is forced off the distal end of the cup 104, by the band applicator 108, onto and around the haemorrhoid.

To help provide an indication to the medical practitioner that the band 106 has been applied, the band applicator 108 is shaped to abut with a proximal face 115 of the cup shaped end 104. The proximal face 115 acts as a stop to prevent distal movement of the band applicator 108 beyond a certain position after the band has been applied. When the band applicator 108 abuts the proximal face 115 of the cup shaped end 104, the medical practitioner will feel resistance in the trigger 118 to give him an indication that the band has been applied.

Once the band has been applied, the trigger is then released by the practitioner. The elastic member 114, which is in a compressed state due to the band applicator 108 being moved distally, provides a biasing force to restore the sleeve and band applicator back to their initial positions. The ligator 100 is then reloaded with a new band 106 for subsequent operation as needed.

To help remove the band 106 from the distal edge of the ligator on operation, a ring shaped indent 109 may be provided on the distal end face of the applicator 108.

The ligator 100 may be connected to a vacuum pump by a hose 120 to allow the haemorrhoid to be sucked into the cup 104 at the distal end of the ligator. The pressure inside the cup 104 in this case is controlled by an interior bore 122 of the inner element which is in fluid communication with both the interior of the cup 104 and the hose 120 connected to the vacuum pump.

To control the pressure inside the cup 104, there is an air hole 124 in the handle 102 of the ligator 100 which the medical practitioner can cover with the thumb of their hand which is operating the ligator. Alternatively, a cover (not shown) may be used to selectively cover the hole 124.

The band 106 shown in FIGS. 1A-1B is attached to the ligator 100 using the magazine reloader 200 shown in FIGS. 2A-2D. The reloader 200 is formed of first and second housing parts 202;204 which are releasably connected to one another by a screw 205.

The reloader 200 comprises four feed chambers 206 each of which houses a band feeder 208 and an expansion cone 210.

The expansion cone 210 comprises a central shaft 212 at one end, and a number of fins 214 at the opposite end which are surrounded by a hollow conical expander wall 216. The fins 214 provide support to the conical expander wall 216 and may take any suitable shape necessary to achieve this supporting effect. They may for instance be formed of a solid cylinder inside the hollow conical expander wall 216. At the end of the inside surface of the expander wall 216, there is a groove 217. The expansion cone 210 is slidable within the feed chamber 206 with the shaft 212 being guided in a channel 218 to keep the expansion cone 210 aligned inside the chamber 206.

Figure 2D:
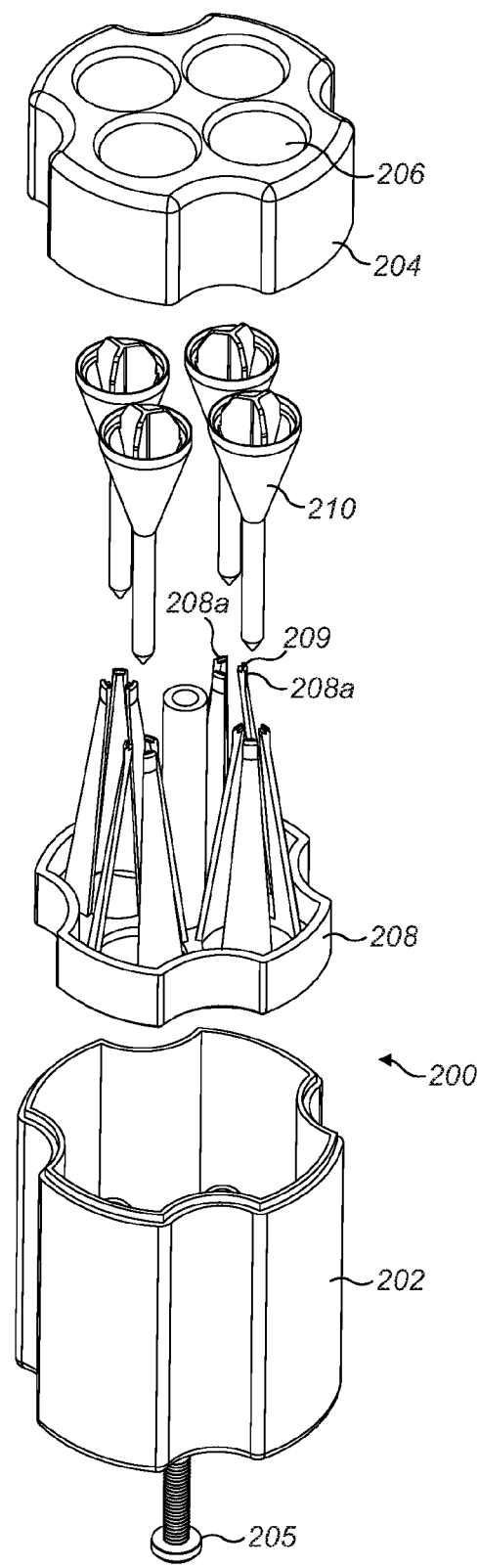

The band feeder 208 shown in FIGS. 2C and 2D has a series of resilient prongs 208a which surround and initially rest on the shaft 212 of the expansion cone 210 at a position close to the narrow end of the conical expander wall 216. The end of each prong 208a which bears on the conical expander wall 216 comprises a foot 209. The feet of the resilient prongs 208a are arranged to support the band 106 whilst it is moved along the conical expander wall 216, and are shaped to prevent the band 106 from passing either underneath or on top of the remaining parts of the resilient prongs 208a. Therefore the feet 209 keep the band 106 in contact with the conical expander wall 216 as the band is pushed.

The reloader 200 is loaded with a band 106 (not shown) positioned around the shaft 212 of the expansion cone 210, and located between the end of the prongs 208a and the apex of the conical expander wall 216 inside the feed chamber 206. The band in this position is unexpanded.

The reloader is assembled as best shown in FIG. 2D. The band feeder 208 is first positioned inside the first housing part 202. A band 106 is then passed around the shaft 212 of each expansion cone 210. Each cone 210 is then inserted through the respective prongs 208a of the band feeder 208 such that the band 106 of each cone rests between the end of the prongs 208a and the apex of the cone's conical expander wall 216. The second housing part 204 is then placed over the expansion cones 210, where it is then fastened to the first housing part 202 by the screw 205.

The reloader 200 is intended to be supplied to a practitioner in a preloaded and sterile state.

Figure 3:
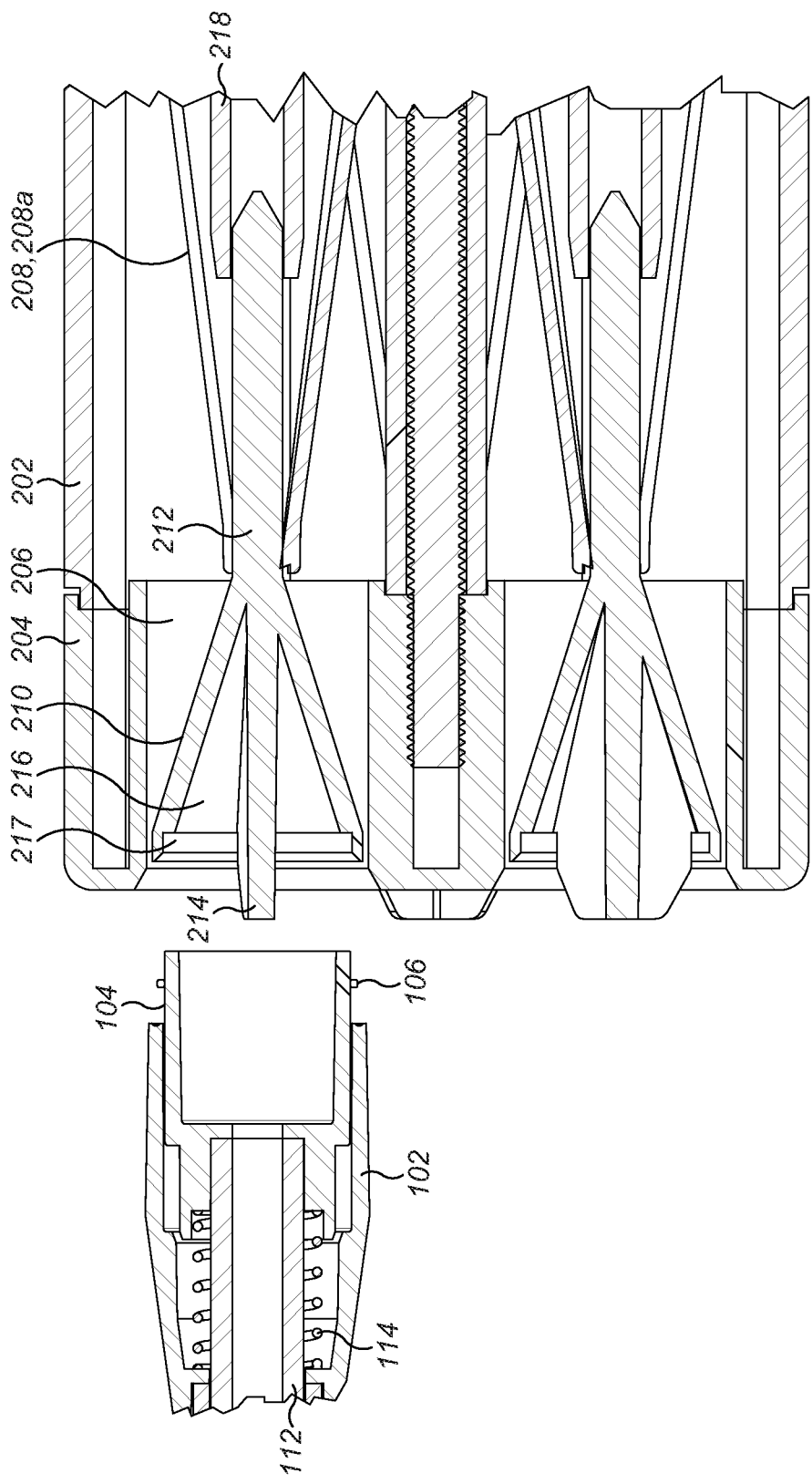
FIG. 3 shows the band ligator in the position for reloading by the reloader.
Figure 4:
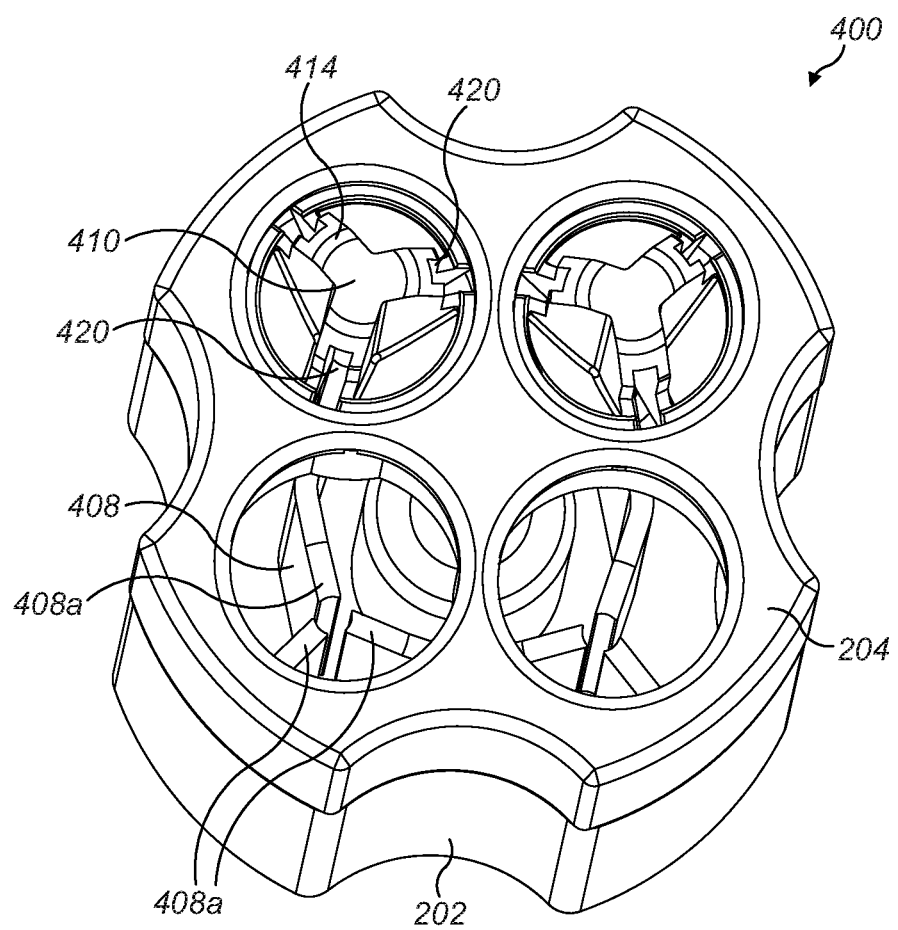
FIG. 4 shows a perspective view of an alternative design of reloader which is configured to be used with the band ligator of FIGS. 1A-1B.

To load the band 106 from the reloader 200 to the ligator 100, the cup 104 of the ligator is placed adjacent to the feed chamber 206 of the reloader 200 as shown in FIG. 3. The outer edge of the cup 104 is then inserted into, and pushed against, the groove 217 causing the expansion cone 210 to move with the cup 104 into the feed chamber 206.

As the expansion cone 210 moves inside the reloader 200, it causes the resilient prongs 208a to deflect outwardly, and the feet 209 of the prongs to push the band 106 along and conical expander wall 216, causing the band to expand as it does so. During this movement, frictional forces between the feet 209 and the conical expander wall 216 prevent the band 106 from passing between the two components. Continued movement of the cup 104 with the expansion cone 210 inside the reloader 200 ultimately results in the band 106 being pushed by the feet 209 of the prongs 208a off the end of the conical expander wall 216 and contracting onto the outer surface of the cup 104.

Once the band 106 is located in this position and loaded on the outside edge 104 of the ligator 100, the ligator can be removed from the reloader 200 by pulling its cup 104 out of the groove 217 of the expansion cone 210.

Once the ligator has been removed, the expansion cone 210 does not return to its starting position. Friction between the prongs 208a and the conical expander wall 216 keeps the expansion cone 210 in place and prevents it from falling out the end of the reloader 200. The advantage of the expansion cone remaining in its final position is that the operator then knows whether or not a band from a particular feed chamber 206 has been used.

Once the loaded band 106 has been applied from the ligator, a further band 106 from one of the other unused feed chambers 206 may be loaded onto the ligator in the same way as discussed above.

From its unexpanded state when housed in the reloader 200 to its expanded state when positioned on the tip of the ligator 100, the diameter of the band 106 may increase from around 3 mm to around 11-13 mm.

Once all the band in the reloader 200 have been used, or all the haemorrhoids on a patient have been banded, the reloader 200 can be either sent away for refilling and re-sterilising, or more preferably disposed of. The ligator 100 can also be re-sterilised for use on a new patient, or more preferably disposed of.

An alternative design to the reloader 200 shown in FIGS. 2A-2D is shown in FIGS. 4 and 5A-5F.

The alternate reloader design may comprise any number of feed chambers 406 for dispensing any number of bands 106. The configuration shown in FIG. 4 has four feed chambers 406, whilst the configuration shown in FIGS. 5A-5F has only one feed chamber 406. Irrespective of the number of feed chambers 406 present, the structure and operation of the reloader shown in FIGS. 4 and 5A-5F is the same. The structure of the alternate reloader design shown in these Figures will now be described.

Unlike in the first reloader design 200, in the alternate reloader 400 the fins 414 of the expansion cone 410 each accommodate a slot 420 which extends from a position near the groove 217 end of the expansion cone 410 down the remaining length of the expansion cone 410. The slot 420 of each fin 414 is configured to accommodate a respective plate 408a of the band feeder 408.

The ends of the plates 408a in this reloader design are responsible for moving the band 106 along the conical expander wall 216 of the expansion cone 410. These ends which come into contact with the band 106 are profiled as shown in FIGS. 4 and 5A-5F to ensure the band is guided as effectively as possible along the conical expander wall 216. As the tip of the ligator is inserted into the reloader, the band moves radially outwards across these ends with the conical expander effectively acting as a cam surface to force the band outwards. This mechanism contrasts with the band moving mechanism in the reloader shown in FIGS. 2A-2D where the band is moved along the conical expander wall 216 by the resilient prongs 208a, which deflect outwardly as the tip of the ligator is inserted into the reloader.

The end of the conical expander wall 216 closest to the base of the expansion cone 410 has an inwardly tapered surface 422.

The remaining parts of the alternate reloader 400 shown in FIGS. 4 and 5A-5F are similar to those of the reloader 200 shown in FIGS. 2A-2D. Accordingly some of the reference numerals from the first reloader 200 have been used in labelling the corresponding features in the alternate reloader 400.

To load a band 106 from the second reloader 400 shown in FIGS. 4 and 5A-5F, the operator uses the ligator 100 in the same way as he would when loading a band 106 from the first reloader 200 shown in FIGS. 2A-2D.

Figure 5A:
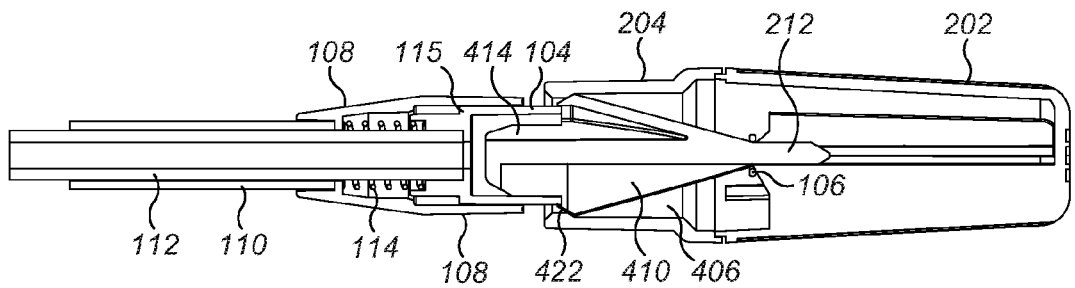
FIGS. 5A-5F show a variant of the alternative design of reloader shown in FIG. 4, which is shown in various positions during the reloading process with the ligator shown in FIG. 1A-1B.
Figure 5B:
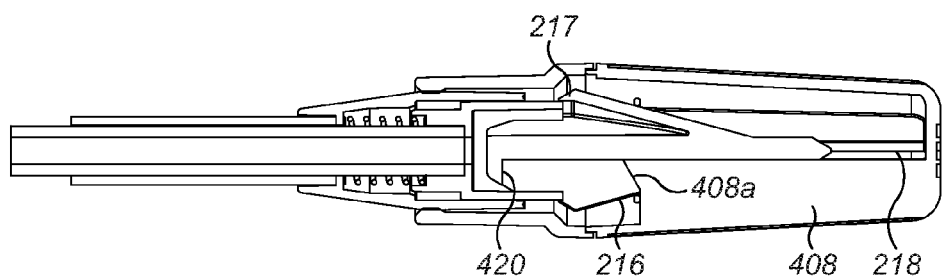
Figure 5C:
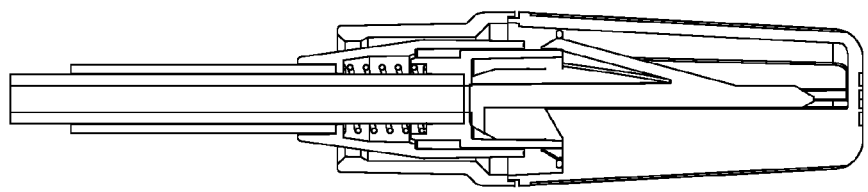
Figure 5D:
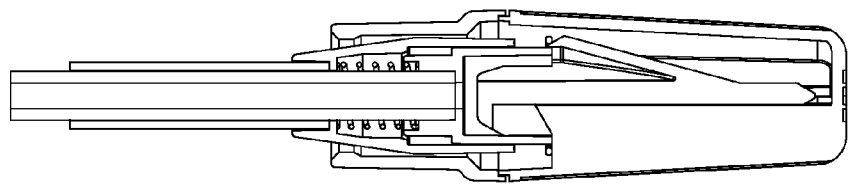
Figure 5E:
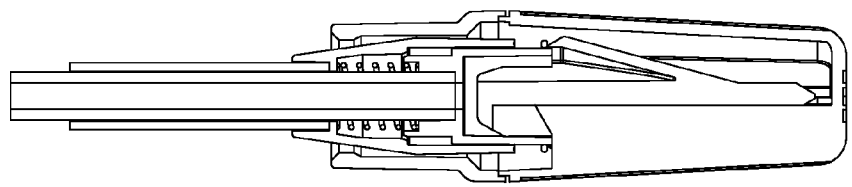
Figure 5F:
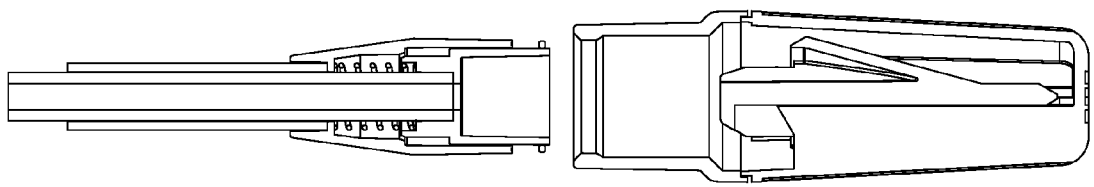

FIGS. 5A-5F shows the band ligator in various positions during the reloading process of the alternate reloader design of FIGS. 4 and 5A-5F. FIG. 5A shows the ligator 100 unloaded whilst FIG. 5F shows the ligator loaded and ready to use.

As the ligator 100 and accordingly the expansion cone 410 moves inside the reloader 400, each plate 408a moves along its respective slot 420 in the expansion cone 410. The plates 408a push the band 106 along the conical expander wall 216, causing the band to expand as it does so, as shown in FIG. 5B. Continued movement of the cup 104 with the expansion cone 410 inside the reloader 400 ultimately results in the band 106 being located in its most stretched condition as shown in FIG. 5C. When the cup 104 is pushed any further into the reloader 400, the band 106 is forced by the plates 408a onto the inwardly tapered surface 422 of the expansion cone 410.

When the band 106 is pushed onto the inwardly tapered surface 422, the band then by its own resilience, and/or by continued pushing of the ligator into the reloader, contracts down the inwardly tapered surface 422 (as shown in FIG. 5D where the band is part way down the taper surface 422) and finally rests on the outer surface of the cup 104 of the ligator 100 (as shown in FIG. 5E).

Once the band 106 is located on the cup of the ligator 100, the ligator is then removed from the reloader 400 and is ready to use (as shown in FIG. 5F).

Figure 6:
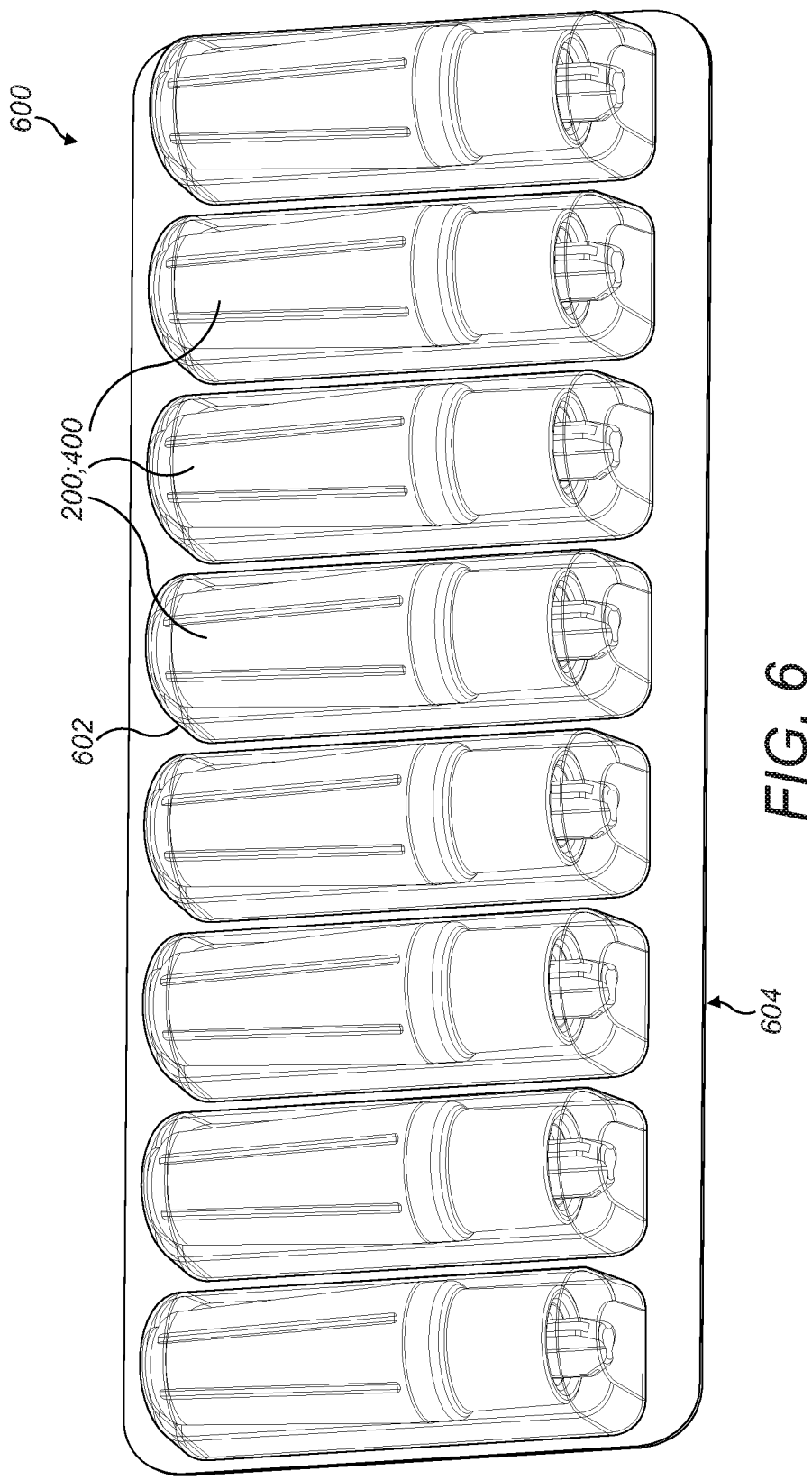
FIG. 6 shows a perspective view of a series of reloaders contained in sterile packaging.

Either the first or second reloaders 200;400 may be accommodated in a sterile pack 600, as shown in FIG. 6, which is configured to store a number of the reloaders each in their own sterile enclosure 602. The rear of the pack 600 is formed of a peelable film 604, which allows selective access to each enclosure 602 containing a reloader 200;400.

The reloaders 200;400 shown in FIG. 6 are single feed chamber 206;406 variants to the reloaders shown in FIGS. 2A-2D and FIG. 4, and each reloader accommodates one band 106. Depending on the number of haemorrhoids to be banded on a patient, the medical practitioner can selectively access the necessary number of reloaders needed by peeling the film 604 as required. Any reloaders 200;400 not accessed in the pack 600 in their sterile containers 602 can be used on subsequent patients.

The invention claimed is:

1. A magazine for dispensing at least one band onto the tip of a haemorrhoid ligator, the magazine comprising:
    a first housing part;
    a second housing part connected to the first housing part;
    a chamber defined by the first and second housing parts and having an open end in the second housing part; and
    an expander housed within the chamber and surrounded by the first and second housing parts; and
    a band positioned around a portion of the expander;
    wherein the expander is actuatable by the tip of the ligator to expand the band and push the band onto the tip of the ligator, while the band is still inside the chamber, and as the tip of the ligator is inserted into the open end of the chamber.

2. The magazine according to claim 1, wherein a plurality of chambers are defined by the first and second housing parts, and wherein each chamber houses a respective expander.

3. The magazine according to claim 1, wherein the expander comprises an expansion cone and a band feeder, wherein the band feeder is arranged to push the band along an outer surface of the expansion cone upon insertion of the tip.

4. The magazine according to claim 3, wherein the band feeder comprises a plurality of resilient prongs, wherein each prong rests against, and is deflected by, the outer surface of the expansion cone as the tip is inserted into the magazine.

5. The magazine according to claim 4, wherein each prong comprises a foot for holding the band as it is pushed, wherein the foot is the part of the prong which rests against the outer surface of the expansion cone.

6. The magazine according to claim 3, wherein the band feeder comprises a plate which is configured to slide with respect to a slot in the expansion cone, the plate having an end which engages with the band as it is pushed.

7. The magazine according to claim 6, wherein the end of the plate is shaped to guide the band along the outer surface of the expansion cone.

8. The magazine according to claim 3, wherein the face of the outer surface of the expansion cone furthest from the band feeder is tapered in an opposing direction to the outer surface of the expansion cone.

9. The magazine according to claim 1 in combination with a sterile package, wherein the magazine is sealed within the sterile package.

* * * * *